United States Patent
Sayles et al.

(10) Patent No.: US 9,744,012 B2
(45) Date of Patent: Aug. 29, 2017

(54) POWER TOOTHBRUSH WITH A MODULATED DRIVE SIGNAL

(71) Applicant: KONINKLIJKE PHILIPS N.V., Eindhoven (NL)

(72) Inventors: Thomas Jackson Sayles, Fall City, WA (US); Sandra Mackay, Issaquah, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/104,687

(22) PCT Filed: Dec. 5, 2014

(86) PCT No.: PCT/IB2014/066615
§ 371 (c)(1),
(2) Date: Jun. 15, 2016

(87) PCT Pub. No.: WO2015/092597
PCT Pub. Date: Jun. 25, 2015

(65) Prior Publication Data
US 2017/0000593 A1    Jan. 5, 2017

Related U.S. Application Data

(60) Provisional application No. 61/918,160, filed on Dec. 19, 2013.

(51) Int. Cl.
*A61C 17/22*  (2006.01)
*A61C 17/34*  (2006.01)
(Continued)

(52) U.S. Cl.
CPC .............. *A61C 17/221* (2013.01); *A46B 9/04* (2013.01); *A46B 15/004* (2013.01);
(Continued)

(58) Field of Classification Search
CPC .............. A61C 17/221; A61C 17/3418; A61C 17/3445; A46B 9/04; A46B 15/004
See application file for complete search history.

(56) References Cited

U.S. PATENT DOCUMENTS 3,588,936 A    6/1971   Duve
5,165,131 A    11/1992  Staar
(Continued)

FOREIGN PATENT DOCUMENTS

JP    2001346816 A    12/2001
TW    201110944 A     4/2011
(Continued)

*Primary Examiner* — Shay Karls

(57) ABSTRACT

A power toothbrush includes a handle portion having a drive system therein for moving a set of bristles with a frequency and amplitude to produce clinically effective cleaning results. A modulation system modulates the drive signal by changing the frequency or duty cycle of the drive signal with a frequency varying modulation signal. The modulation frequency will increase from the start to the conclusion of a brushing event for cognitive stimulation while the modulation frequency will decrease between the start and conclusion of a brushing event for cognitive relaxation.

7 Claims, 3 Drawing Sheets

(51) Int. Cl.
*A46B 9/04* (2006.01)
*A46B 15/00* (2006.01)
*A61M 21/00* (2006.01)

(52) U.S. Cl.
CPC ...... *A61C 17/3418* (2013.01); *A61C 17/3445* (2013.01); *A61C 17/3481* (2013.01); *A61M 21/00* (2013.01); *A61C 17/3436* (2013.01); *A61C 17/3463* (2013.01); *A61M 2021/0022* (2013.01)

(56) References Cited

U.S. PATENT DOCUMENTS

| | | | |
|---|---|---|---|
| 5,378,153 A | 1/1995 | Giuliani et al. | |
| 8,769,753 B2 * | 7/2014 | Fraser | A61C 17/20 15/167.1 |
| 2009/0241276 A1 * | 10/2009 | Hall | A61C 17/32 15/22.1 |
| 2010/0237720 A1 | 9/2010 | Taylor | |

FOREIGN PATENT DOCUMENTS

| | | |
|---|---|---|
| TW | 201200701 A | 1/2012 |
| TW | M43236 U | 7/2012 |
| WO | 2007097886 A2 | 8/2007 |
| WO | 2009151461 A1 | 12/2009 |

* cited by examiner

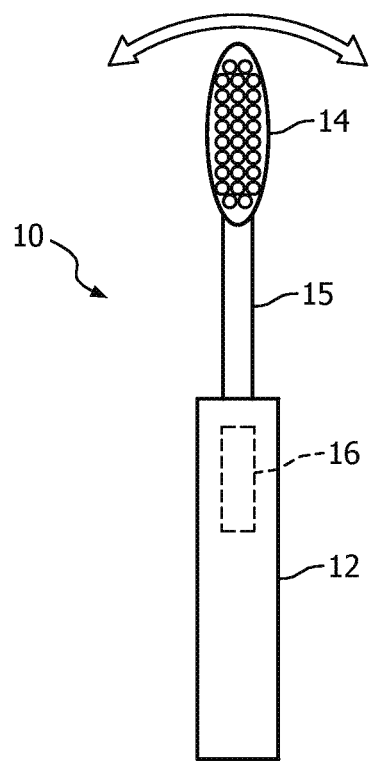
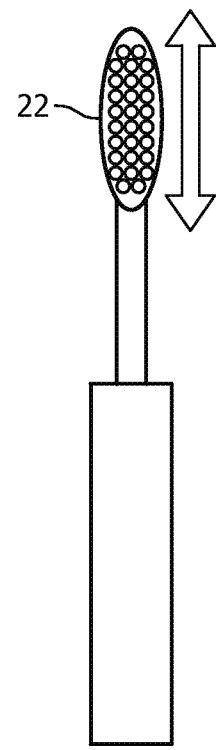
FIG. 1A  FIG. 1B
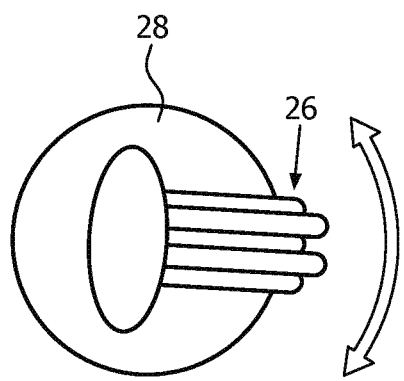
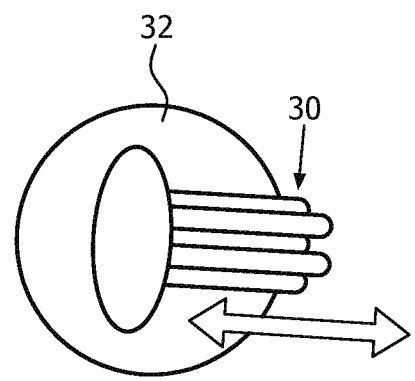
FIG. 1C  FIG. 1D

POWER TOOTHBRUSH WITH A MODULATED DRIVE SIGNAL

CROSS-REFERENCE TO PRIOR APPLICATIONS

This application is the U.S. National Phase application under 35 U.S.C. §371 of International Application No. PCT/IB2014/066615, filed on Dec. 5, 2014, which claims the benefit of U.S. Provisional Patent Application No. 61/918,160, filed on Dec. 19, 2013. These applications are hereby incorporated by reference herein.

TECHNICAL FIELD

This invention relates generally to power toothbrush appliances which have a drive signal in the sonic frequency range, and more specifically concerns such an application where the drive signal varies in frequency or duty cycle.

BACKGROUND OF THE INVENTION

Many power toothbrushes include multiple brushing modes or routines. Typically, these modes focus on various types of dental care needs, such as regular or gentle brushing, oral massage and gum care/stimulation, among others. Oral care with a power toothbrush occurs in both the morning and evening. Such oral care is also often a part of a more detailed personal routine which results in falling asleep in the evening and waking up in the morning. There is an interest in not only improving oral care at these times, but also for decreasing restlessness before falling asleep and for becoming alert after waking up before beginning daily activities.

Accordingly, it would be desirable for a power toothbrush to have a capability to impact the user's attention and provide mental/cognitive stimulation and/or mental/cognitive relaxation.

BRIEF DESCRIPTION OF THE DRAWINGS

FIGS. 1A-1D are simplified views of several brushing motions of a power toothbrush brushhead.

SUMMARY OF THE INVENTION

Figure 2C:
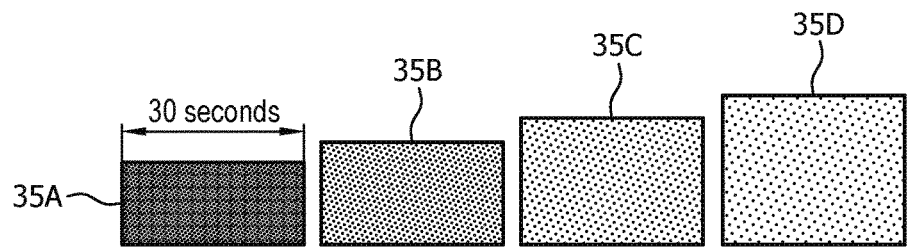
FIGS. 2A-2C show modulation diagrams for a drive signal which provides cognitive stimulation and an assist in waking up.

Accordingly a power toothbrush, comprises a handle portion; a brushhead assembly having a set of bristles at a distal end thereof; a drive system for moving the set of bristles with a motion having a frequency in the sonic range and an amplitude in a range to produce clinically effective cleaning of a user's teeth; and a modulation system for changing the frequency and/or duty cycle of the drive signal to produce a cognitive effect in addition to clinically effective teeth cleaning.

BEST MODE FOR CARRYING OUT THE INVENTION

FIGS. 1A-1D show in simplified form a power toothbrush which produces various bristle motions. FIG. 1A shows a power toothbrush 10 with a handle 12 and a brushhead 14 mounted on the distal end of a neck 15, which rotates through a specific angle, at a specified frequency. The brushhead is driven by a drive system 16 contained within a handle portion 14. The brushing illustrated in FIG. 1A is a side to side rotation, about a longitudinal axis of the appliance. Another brushing motion is shown in FIG. 1B in which the brushhead 22 moves in an in-and-out axial direction, producing a back-and-forth motion along the teeth. FIG. 1C is an end view of a brushhead 26 on a neck (not visible) extending from a handle 28, in which the bristles move in a sweeping-type motion. FIG. 1D is an end view of a brushhead 30 mounted on a neck (not visible) which extends from a handle 32, with the bristles moving in a tapping-type action, perpendicular to the longitudinal axis of the appliance, toward and away from the teeth. Such single motions can be accomplished by a variety of drive systems. One example for the sweeping motion is disclosed in U.S. Pat. No. 5,378,153, the contents of which are hereby incorporated by reference. Typically, for effective cleaning the power toothbrush operates in the sonic frequency range, in the range of 130-150 Hz, but also a wider frequency range of between 40 and 500 Hz. The bristle tip amplitude of movement will typically be between 0.5 mm and 6.6 mm, with a preferred amplitude of approximately 3.5 mm. Further, the bristle tip velocity will be greater than 1.5 meters per second, between 1.5 and 2.0 meters per second.

Figure 2A:
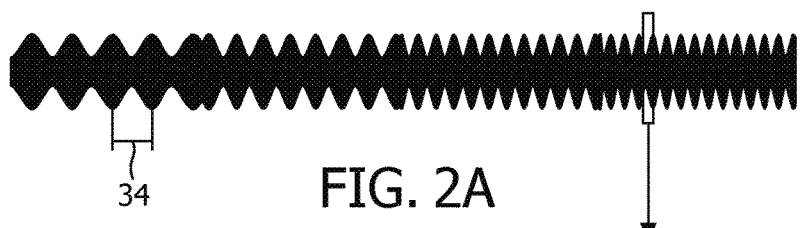
Figure 2B:
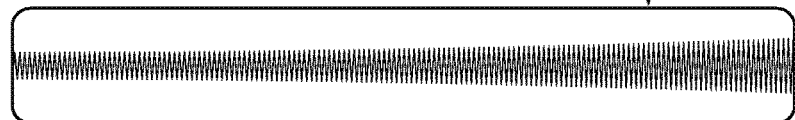

In the present invention, the drive signal for the power toothbrush is modulated so as to have either a cognitive stimulation or cognitive relaxation effect. FIGS. 2A and 2B shows aspects of modulation of the drive signal to produce cognitive stimulation, with the modulation period (1/modulation frequency) shown at 34 in 2A, while FIG. 2B is a frequency diagram showing an increase in frequency of the brushhead movement due to the modulation of FIG. 2A. The modulation increases in frequency during the two-minute brushing event. The range of change will be from 0.2 Hz to 100 Hz. In one specific example, the modulation frequency increases every 30 seconds during the typical use period. As one example, in the first period, the modulation frequency will be 0.5 Hz; in the second period, the modulation frequency will be 0.75 Hz; in the third period, the modulation frequency will be 1.5 Hz; and in the fourth period, the modulation frequency will be 3 Hz. FIG. 2C shows the result of an increase in frequency every 30 seconds, referenced at 35A, 35B, 35C and 35D, which is a perceived increase in intensity by the user, producing a cognitive stimulation and an increase in wakefulness, i.e. a wake-up type modulation.

Other modulation patterns similar to the above can be used. Further, more complex modulation patterns can be used, including variable tones over the two minute brushing event or during portions of each brushing event, either at 30 second intervals or at other times. This can include variable tones, rhythms, or other audible sounds. As discussed above, such a pattern will result in a perceived increase in power during the four periods. Typically, for cognitive stimulation, the modulation frequency will increase over the entire brushing event in frequency, although the frequency may vary to some extent during any one particular period.

Figure 3C:
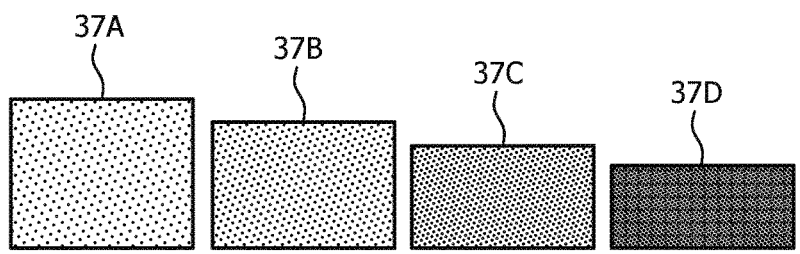
FIGS. 3A-3C show modulation diagrams for a drive signal which produces mental relaxation and an assist in falling asleep.
Figure 3A:
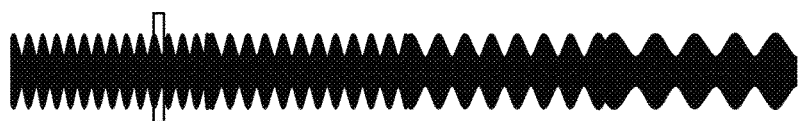
Figure 3B:
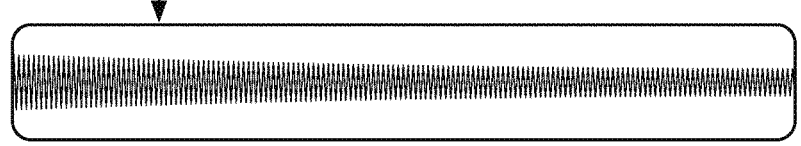

FIGS. 3A-3C illustrate the modulation pattern of a drive signal which produces a cognitive relaxation. In this case, referring to FIG. 3A, the modulation period will begin the brushing event at a relatively lower value, and the modulation frequency at a higher value than at the conclusion of the brushing event, with a high value of 100 Hz to a low value of 0.2 Hz. At specific times within the two-minute brushing event, e.g. every 30 seconds, the modulation frequency will decrease, producing a change in the sonic effective frequency of the brushhead as shown in FIG. 3B. One specific example will be an initial modulation frequency of 3 Hz for the first 30 seconds; a modulation frequency in a second 30 second period of 1.5 Hz; a modulation frequency in a third 30 second period of 0.75 Hz; and a modulation frequency in the fourth 30 second period of 0.5 Hz. These specific frequencies in the four periods can be varied; the modulation frequency can also vary during each 30 second period; the individual period times may also be varied. However, the overall effect should be a decrease in modulation frequency between the start of the brushing event and the conclusion of the brushing event. This results in a decrease in perceived power intensity between the start or conclusion of the brushing event, as shown in FIG. 3C, 37A-37D. This results in a cognitive relaxation effect, as would be helpful in falling asleep.

Figure 4:
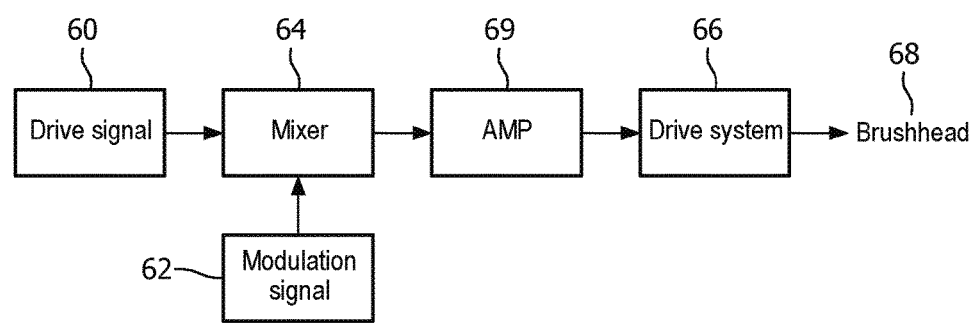
FIG. 4 is a partial block diagram of one embodiment for producing the modulated drive signal of FIGS. 2A and 3A.

FIG. 4 shows, in a simplified view, one system for producing the modulated drive signal described above. FIG. 4 shows the source of a drive signal 60, designed to produce a clinically effective brushing effect, and a source of a modulation signal 62. Again, the modulation signal 62 could be that specifically shown in FIGS. 2A and 3A, or it could be some other modulation signal. Typically, as explained above, the modulation signal will generally follow an increasing frequency pattern to produce cognitive stimulation or a generally decreasing frequency pattern to produce cognitive relaxation. The modulation signal from source 62 and the drive signal from source 60 are applied to an audio mixer 64, which produces the modulated signal for the drive system 66, after being applied to amplifier 69. The resulting signal drives brushhead 68 for various single motion embodiments, such as shown in FIGS. 1A and 1D, depending on the particular drive system used. The signal is amplified to produce a brushhead amplitude of between 0.5 mm and 6 mm, at a velocity of at least 1.5 m/s.

Figure 5:
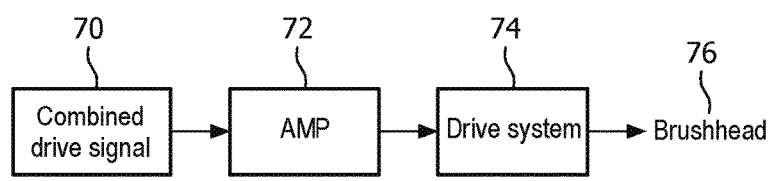
FIG. 5 is a partial block diagram of a second embodiment for producing the modulated drive signal for FIGS. 2A and 3A.

FIG. 5 shows an alternative embodiment, in which a digital recording of a combined drive signal is shown at 70. The digital recording includes a strong signal having an effective sonic frequency, such as between 40-500 Hz, combined with other varying tones, rhythms or audio sounds. This combined drive signal is then applied to an amplifier 72 and then to a drive system 74, which in turn drives a brushhead 76 in a single motion, as shown in FIGS. 1A-1D. The combined drive signal is amplified to achieve the desired bristle tip amplitudes between 0.5 mm and 6.6 mm, with a bristle tip velocity of 1.5 meters per second.

While the modulation described above changes the frequency of the drive signal, the modulation could also similarly be used to change the duty cycle of the drive signal.

Hence, a new power toothbrush has been described which includes a drive signal for a power toothbrush to produce a single brushhead motion which is modulated to change the frequency or the duty cycle of the drive signal to produce either a cognitive stimulating effect or a cognitive relaxation effect.

Although a preferred embodiment of the invention has been disclosed for purposes of illustration, it should be understood that various changes, modifications and substitutions may be incorporated in the embodiment without departing from the spirit of the invention, which is defined by the claims which follow.

What is claimed is:

1. A power toothbrush, comprising:
a handle portion;
a brushhead assembly having a set of bristles at a distal end thereof;
a drive system responsive to a drive signal for moving the set of bristles with a motion having a frequency in the sonic range and an amplitude in a range to produce clinically effective cleaning of a user's teeth during a brushing event; and
a modulation system that comprises a drive signal source, a modulation signal source and an audio mixer coupled to the drive signal source and the modulation signal source for outputting a combined modulation drive signal for changing a frequency of the drive signal, wherein responsive to the combined modulation drive signal, the drive system further moves the set of bristles for producing at least one of a cognitive stimulation or relaxation effect during the brushing event in addition to the clinically effective teeth cleaning, wherein (i) for the cognitive stimulation effect, the combined modulation drive signal increases in frequency at pre-determined intervals from a start of the brushing event to an end of the brushing event, and (ii) for the cognitive relaxation effect, the combined modulation drive signal decreases in frequency at pre-determined intervals between the start and end of the brushing event,
wherein a frequency of a modulation signal from the modulation signal source changes between a lower modulation frequency of 0.2 Hz and an upper frequency of 100 Hz.

2. The power toothbrush of claim 1, wherein the frequency range of the drive signal is approximately 50-500 Hz.

3. The power toothbrush of claim 1, wherein the amplitude range is approximately 0.5 mm and 6.6 mm.

4. The power toothbrush of claim 1, wherein a frequency of a modulation signal from the modulation signal source changes at specified time periods during the brushing event.

5. The power toothbrush of claim 1, wherein a frequency of a modulation signal from the modulation signal source changes between a lower modulation frequency of 0.2 Hz and an upper frequency of 100 Hz.

6. The power toothbrush of claim 1, wherein the brushhead assembly has a single motion.

7. A power toothbrush, comprising:
a handle portion;
a brushhead assembly having a set of bristles at a distal end thereof;
a drive system responsive to a drive signal for moving the set of bristles with a motion having a frequency in the sonic range and an amplitude in a range to produce clinically effective cleaning of a user's teeth during a brushing event; and
a modulation system that comprises a drive signal source, a modulation signal source and an audio mixer coupled to the drive signal source and the modulation signal source for outputting a combined modulation drive signal for changing a duty cycle of the drive signal, wherein responsive to the combined modulation drive signal, the drive system further moves the set of bristles for producing at least one of a cognitive stimulation or relaxation effect during the brushing event in addition to the clinically effective teeth cleaning, wherein (i) for the cognitive stimulation effect, the combined modulation drive signal increases the duty cycle at pre-determined intervals from a start of the brushing event to an end of the brushing event, and (ii) for the cognitive relaxation effect, the combined modulation drive signal decreases the duty cycle at pre-determined intervals between the start and end of the brushing event.

\* \* \* \* \*